United States Patent
Inoue

(10) Patent No.: US 7,033,482 B2
(45) Date of Patent: Apr. 25, 2006

(54) SELF-DIAGNOSTIC METHOD FOR ELECTROCHEMICAL GAS SENSOR AND GAS DETECTING DEVICE

(75) Inventor: Tomohiro Inoue, Monoo (JP)

(73) Assignee: Figaro Engineering Inc., Osaka (JP)

( * ) Notice: Subject to any disclaimer, the term of this patent is extended or adjusted under 35 U.S.C. 154(b) by 0 days.

(21) Appl. No.: 11/025,992

(22) Filed: Jan. 3, 2005

(65) Prior Publication Data

US 2005/0121338 A1 Jun. 9, 2005

Related U.S. Application Data

(63) Continuation of application No. PCT/JP04/12257, filed on Aug. 26, 2004.

(51) Int. Cl.
*G01N 27/404* (2006.01)
(52) U.S. Cl. .................. 205/775; 204/401; 204/432; 73/1.06
(58) Field of Classification Search ............... 204/401, 204/432; 205/775, 783; 73/1.06; 702/104
See application file for complete search history.

(56) References Cited

U.S. PATENT DOCUMENTS

| | | | |
|---|---|---|---|
| 5,020,499 A | * | 6/1991 | Kojima et al. ............... 123/479 |
| 5,423,963 A | * | 6/1995 | Fletcher et al. ............ 205/782.5 |
| 5,733,436 A | * | 3/1998 | Demisch et al. ............. 205/775 |
| 6,200,443 B1 | | 3/2001 | Shen et al. |

OTHER PUBLICATIONS

Toxic Gas CiTiceLs, product catalog from City Technology Ltd, pp. 2-39, dated prior to Jul. 30, 1999.*
Patent Abstract for JP 2004-61171, Feb. 26, 2004.*
Patent Abstract for JP 2000-146906, May 26, 2000.*
Patent Abstract of JP 61-212753, Sep. 20, 1986.*
Patent Abstract for JP -4-190154, Jul. 8, 1992.*

* cited by examiner

*Primary Examiner*—Kaj K. Olsen
(74) *Attorney, Agent, or Firm*—Rothwell Figg Ernst & Manbeck

(57) ABSTRACT

An electrochemical gas sensor is self-diagnosed on the basis of an output waveform that is generated when a power source of said gas sensor is turned on after said power source has been turned off for a short time and an output waveform that is generated when said power source is turned on after said power source has been turned off for a long time. In a normal gas sensor, when the power source is turned on after the power source has been turned off for the short time, a bottom will be generated in the potential of the sensing electrode side, and when the power source is turned on after the power source has been turned off for the long time, a peak will be generated in the potential of the sensing electrode side.

A self-diagnosis of the electrochemical gas sensor can be done without pulse power source for self-diagnosis, and the dead time from self-diagnosis until start of detection can be shortened.

17 Claims, 12 Drawing Sheets

1) S1

2) S2

3) Sensor Output (Short Break)

4) Sensor Output (Long Break)

SELF-DIAGNOSTIC METHOD FOR ELECTROCHEMICAL GAS SENSOR AND GAS DETECTING DEVICE

CROSS REFERENCE TO RELATED APPLICATION

This application is a continuation of PCT/JP04/12257 filed Aug. 26, 2004, and designating the U.S.

FIELD OF THE INVENTION

This invention relates to self-diagnosis for an electrochemical gas sensor using electrolyte such as proton conductor or liquid electrolyte.

BACKGROUND ART

U.S. Pat. No. 5,650,054 describes the structure of a proton conductor gas sensor. In this gas sensor, a lower part of a metal can is used as a water reservoir, and the body of a CO sensor is held in an upper part thereof with a necked part in between. The body of the CO sensor comprises an MEA comprising a proton conductive membrane and electrodes on the front face and the back face thereof, and porous carbon sheets for gas dispersion also serving as electron-conductive contacts. The bottom of the sensor body is made to contact a metal washer having a water vapor introducing hole, and the upper part thereof is made to contact a metal washer having a dispersion control hole. The washer at the bottom is held by a constricted part of the metal can, a gasket is provided between the upper washer and the metal can, the upper part of the metal can is narrowed down to fit the upper and lower metal plates (washers) and the sensor body held between them in the metal can. The sensor body is held by the pressure due to narrowing, and connection between the upper and lower metal plates and the carbon sheets of the sensor body is also maintained by the pressure.

Self-diagnosis of proton conductor gas sensor is proposed by, for example, U.S. Pat. No. 6,200,443. Weak voltage pulses are applied between the sensing electrode and the counter electrode of a gas sensor for a short time, and the capacitance after turning off the pulses is measured. It is claimed that the capacitance of a normal sensor and that of a defective sensor differ from each other, hence self-diagnosis can be done. However, as the internal resistance of electrochemical gas sensors is low, being ohm order. When a voltage is applied between the two electrodes, even if they are weak pulses for a short period, there are possibilities of changes in the electrolyte or the electrodes and generation of hysteresis. Moreover, a pulse power source is needed for self-diagnosis, and detection can not be done until elimination of the hysteresis after application of pulses.

Document 1: U.S. Pat. No. 5,650,054
Document 2: U.S. Pat. No. 6,200,443

SUMMARY OF THE INVENTION

Object of the Invention

Preferably, the step for self-diagnosing has a step for judging the gas sensor normal when the output peak is present and for judging the gas sensor defective when the output peak is not present.

Particularly preferably, at a first frequency, the method performs the step for opening the connection for a period shorter than a predetermined period, performs the step for reconnecting the sensing electrode and the counter electrode, and performs the step for self-diagnosing the gas sensor according to whether the output bottom is present, and at a second frequency lower than the first frequency, performs the step for opening the connection for a period longer than the predetermined period, performs the step for reconnecting the sensing electrode and the counter electrode, and performs the step for self-diagnosing the gas sensor according to whether the output peak is present.

In this invention, the gas detecting device comprising an electrochemical gas sensor having an electrolyte, a sensing electrode, and a counter electrode, the sensing electrode and the counter electrode being connected via an amplifying circuit, the gas detecting device further comprises: a switch opening and closing the connection between the sensing electrode and the counter electrode; self-diagnostic means for making the switch open, making the switch close, detecting a peak or a bottom in the output of the amplifying circuit, and judging the gas sensor normal when the bottom or the peak is detected and judging the gas sensor defective when the bottom or the peak is not detected; and display means for displaying the judgement.

Preferably, the self-diagnostic means makes the switch open for a period longer than a predetermined period, makes the switch close, judges the gas sensor normal when the output peak is detected, and judges the gas sensor defective when the output peak is not detected.

Particularly preferably, self-diagnostic means has: means for making, at a first frequency, the switch open for a first period shorter than a predetermined period and the switch close; and at a second frequency lower than the first frequency, the switch open for a second period longer than the predetermined period and the switch close, and the self-diagnostic means judges the gas sensor according to whether the output bottom is present after the first period, and further judges the gas sensor according to whether the output peak is present after the second period.

Preferably, the switch is a power switch of the amplifying circuit or a switch electrically connecting and disconnecting the gas sensor to the amplifying circuit.

In this specification, an output of the electrochemical gas sensor or the amplifying circuit is defined to be positive (+) when the current flows from the sensing electrode to the counter electrode in the sensor and to be negative (−) when the current flows from the counter electrode to the sensing electrode. An output is +corresponds the presence of CO, H2, etc., for example, if CO is present, a reaction

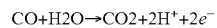

will proceed at the sensing electrode, and a reaction

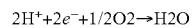

proceeds at the counter electrode. Accordingly, an output peak has the same direction as an output when the sensor contacts a reducing gas, and an output bottom has the same direction as an output when the counter electrode and the sensing electrode are set reversely to the incidental circuit and CO is present, in other words, it has the direction of an output when a reducing gas concentration becomes negative. In the embodiment, a specific structure of the gas sensor, specific materials of the electrolyte and electrodes, and specific amplifying circuit are described, but all of them are discretionary.

For example, either the sensing electrode or the counter electrode is connected to one input of an operational amplifier; the other is connected to the other input of the operational amplifier, and then, the sensing electrode and the counter electrode will be connected to each other via the operational amplifier.

ADVANTAGES IN THE INVENTION

According to the present invention, an electrochemical gas sensor is self-diagnosed on the basis of its output waveform that is generated when the connection between the sensing electrode and the counter electrode of the gas sensor is connected again after the connection has been opened. Accordingly, a special power source for self-diagnosis is not needed, and as no voltage is applied between the sensing electrode and the counter electrode of the gas sensor, there is no possibility of degrading the sensor with voltage pulses for self-diagnosis. In the experiments made by the present inventor, the dead time from reconnecting the sensing electrode and the counter electrode until detection can be made again is, for example, not more than 20 seconds. Thus the dead time due to self-diagnosis can be made shorter in comparison with the case of applying voltage pulses. Self-diagnosis of the present invention can detect defective contact between external terminals and the sensing electrode and the counter electrode, breaking, short-circuit, and degradation in sensor sensitivity, shifting of zero gas level to an abnormal position, etc.

The transient waveforms that were generated when the sensing electrode and the counter electrode were connected again are of two kinds. When the connection was opened for a short time, for example, one minute or less, and then it was reconnected, an output bottom was observed. In contrast to it, when the connection was opened for a long time, for example, five minutes or over, and then it was reconnected, an output peak was detected. An output bottom after opening the connection for a short time was also observed in gas sensors of poor sensitivity, and it was difficult to distinguish normal gas sensors from gas sensors of poor sensitivity. However, simple defects such as breaking or short-circuit were detected reliably. Next, with regard to the output peak after opening the connection for a long time, normal gas sensors and gas sensors of poor sensitivity were distinguished successfully. In this case, generation of an output peak was limited to normal gas sensors. An output peak was not generated when poor sensitivity, shifting of zero gas level, breaking or short-circuit was present.

Accordingly, if the characteristics when the connection is reclosed after the connection has been opened for a short time or a long time, namely, the presence or absence of a bottom or a peak is used, simple defects such as breaking or short-circuit can be detected reliably, and poor sensitivity or the like can be detected to some extent. If an output peak after opening the connection for a long time is used, poor sensitivity, etc. can be detected reliably. If the connection is opened for a long time, the dead time of detection will get longer. Hence self-diagnosis using opening for a long time is used at a second frequency that is low, such as once a month, and self-diagnosis using opening for a short time is used at a first frequency that is high such as once a day, self-diagnosis can be done reliably. Repetition of the mode of opening for a short time can also increase the reliability of detection.

When the gas detecting device is driven by a battery power source, to save electric power, it is practiced to start up the amplifying circuit and the microcomputer for signal processing every predetermined period and suspend their operation in the remaining time. Accordingly, if the connection between the sensing electrode and the counter electrode is broken by turning off the power source of the amplifying circuit and the connection between the sensing electrode and the counter electrode is closed by turning on the power source thereof, self-diagnosis can be done by utilizing turning on and off of the amplifying circuit.

Figure 1:
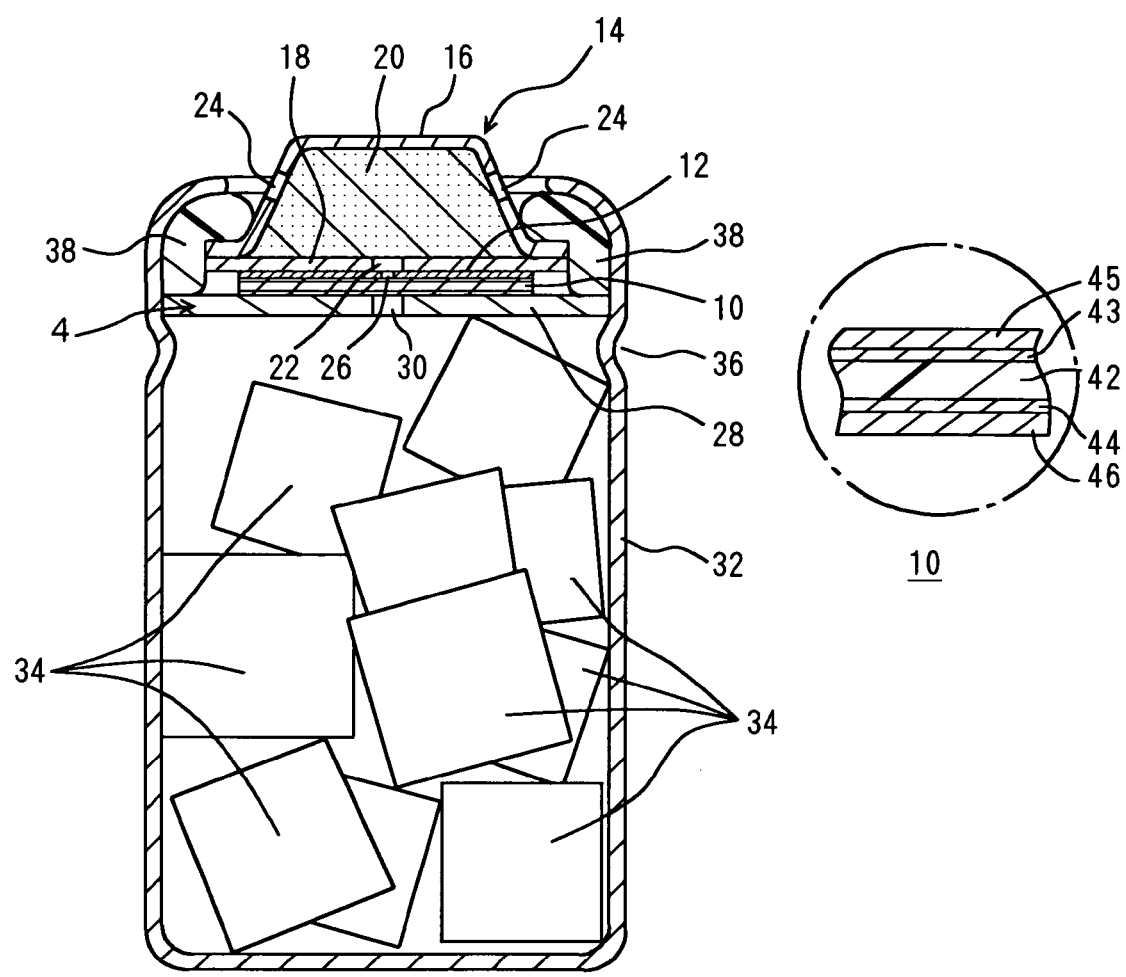
[FIG. 1] A sectional view of an electrochemical gas sensor.

BRIEF DESCRIPTION OF SYMBOLS 2 electrochemical gas sensor
4 sensor body
10 MEA
12 diffusion control plate
14 upper housing
16 cap
18 bottom plate
20 filter material
22, 24 opening
26 diffusion control hole
28 washer
30 water vapor introducing hole
32 metal can
34 gel
36 concave
38 gasket
42 proton conductive membrane
43 sensing electrode
44 counter electrode
45, 46 electron-conductive carbon sheet
50 power source
51 reset switch
54 microcomputer
55 AD converter
56 CO detector
57 self-diagnosis part
58 power controller
59 LED drive
60 LED group
61 buzzer drive
62 buzzer
63 LCD drive
64 LCD
65 EEPROM
66 reset controller
67 battery checker
68 timer
69 RAM
R1–R10 resister
C1–C5 capacitor
IC1–IC3 operational amplifier
S1–S4 switch
+Vcc circuit power source

EMBODIMENTS

Embodiments of the present invention will be described below.

EMBODIMENT

Figure 2:
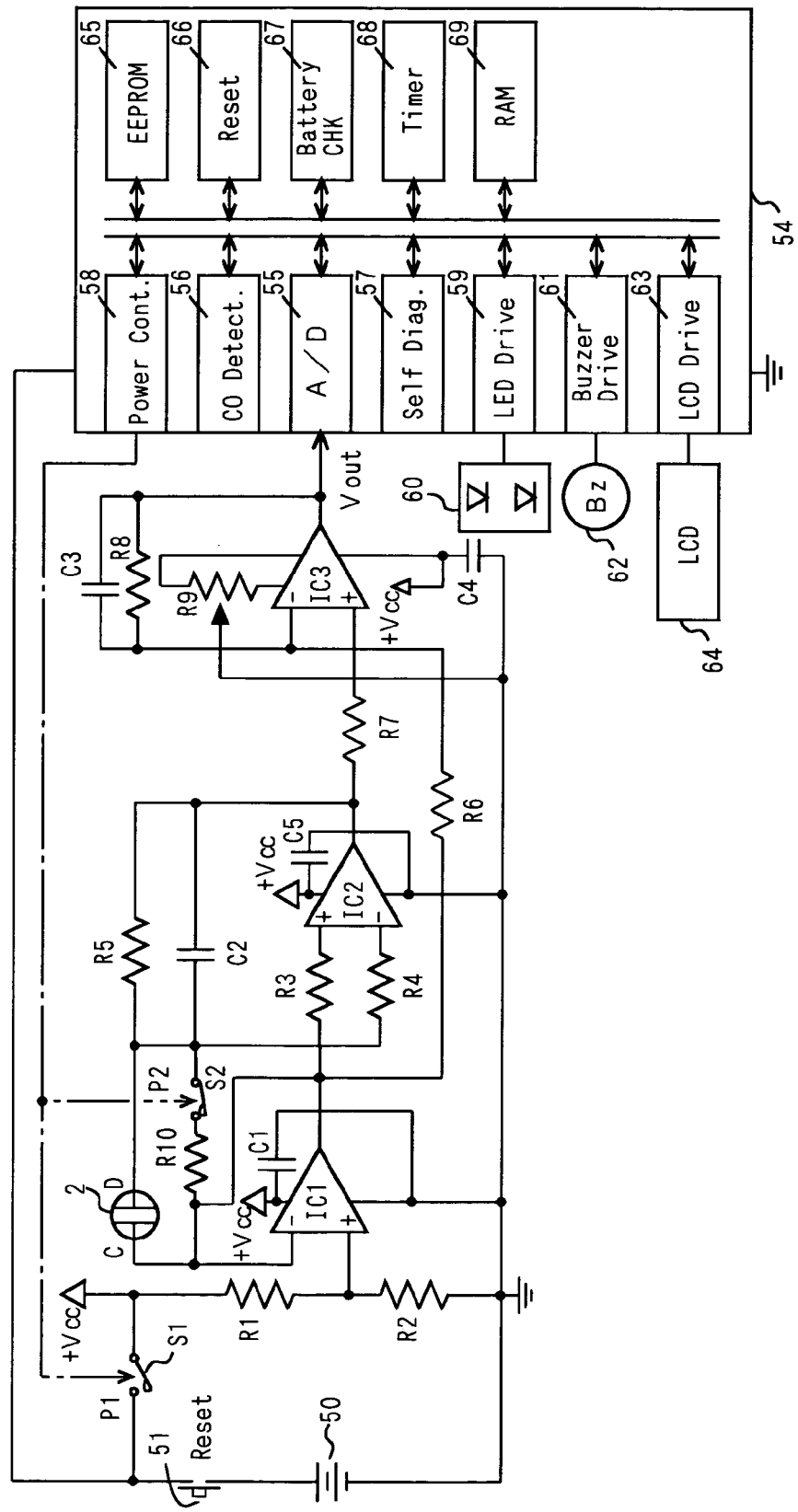
[FIG. 2] A block diagram of an electrochemical gas detecting device.
Figure 3:
[FIG. 3] An operating waveform diagram of the electrochemical gas detecting device. 1) illustrates the operation of a switch S1, 2) illustrates the operation of a switch S2, 3) illustrates self-diagnosis based on presence/absence of a bottom after opening the switch S1 for a short period, and 4) illustrates self-diagnosis based on presence/absence of a peak after opening the switch S1 for a long period.
Figure 3:
Figure 3:
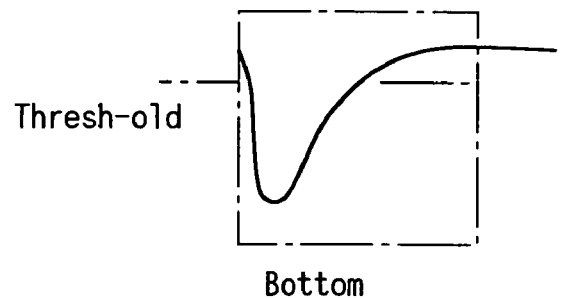
Figure 3:
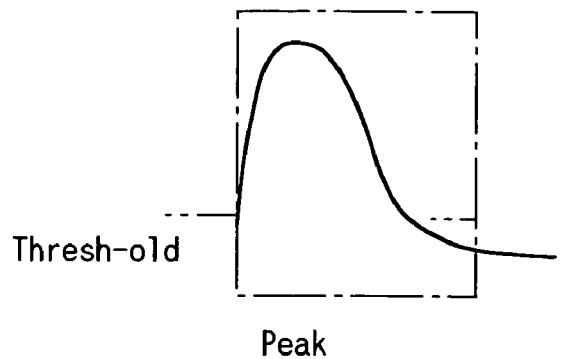
Figure 4:
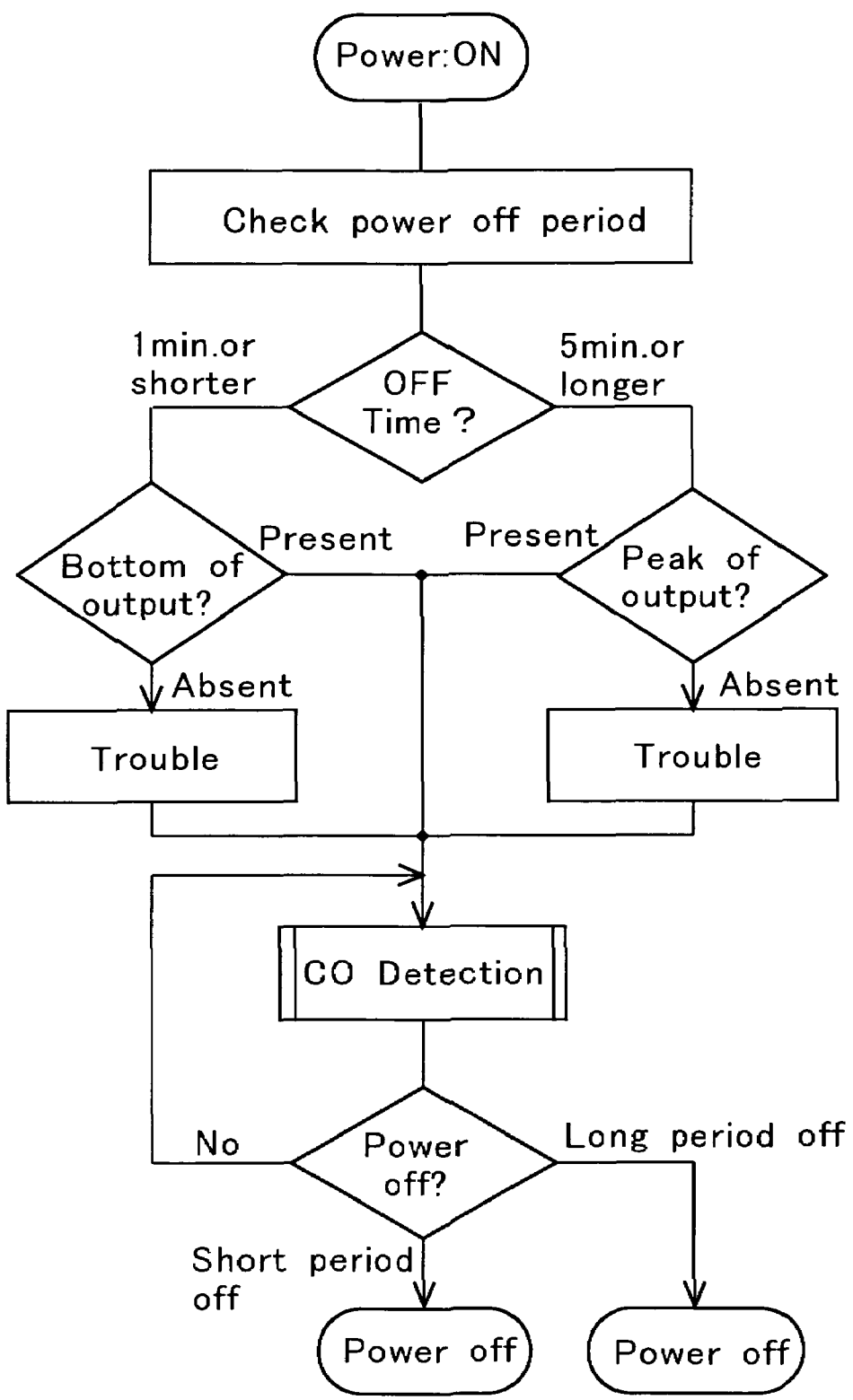
[FIG. 4] A flow chart of the self-diagnosis algorithm of the electrochemical gas sensor.

FIG. 1 illustrates the structure of a proton conductor gas sensor 2 being an example of the electrochemical gas sensor. FIG. 2 is a block diagram of a gas detecting device using the gas sensor 2, and FIG. 3 is the operation waveform diagram thereof. FIG. 4 is a flow chart illustrating the self-diagnosis algorithm of the electrochemical gas sensor. In this embodiment, a power switch S1 is used as a switch for manipulating the connection between the sensing electrode D and the counter electrode C of the gas sensor 2. When the switch S1 is turned off, the connection between the sensing electrode D and the counter electrode C will be broken, and when the switch S1 is turned on, these electrodes will be connected.

Figure 5:
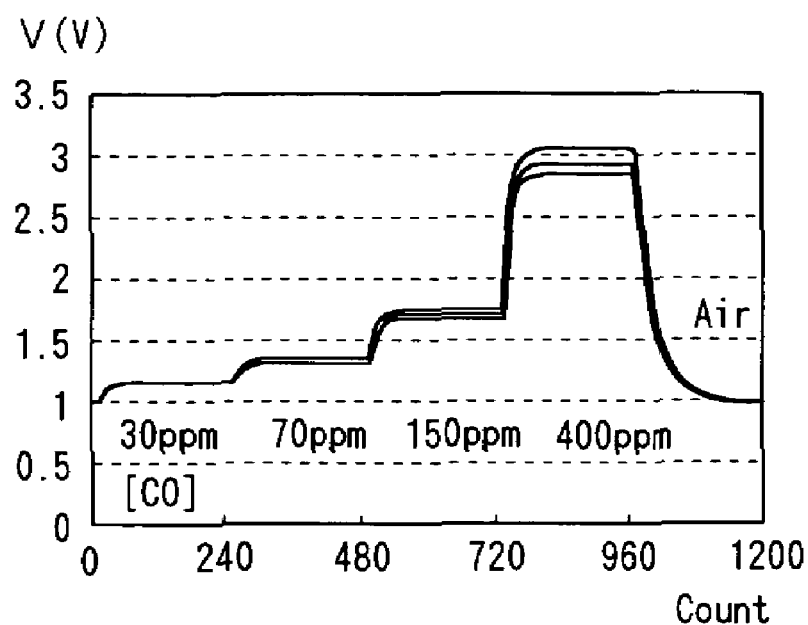
[FIG. 5] A diagram illustrating the sensitivity characteristics of a normal electrochemical gas sensor.
Figure 6:
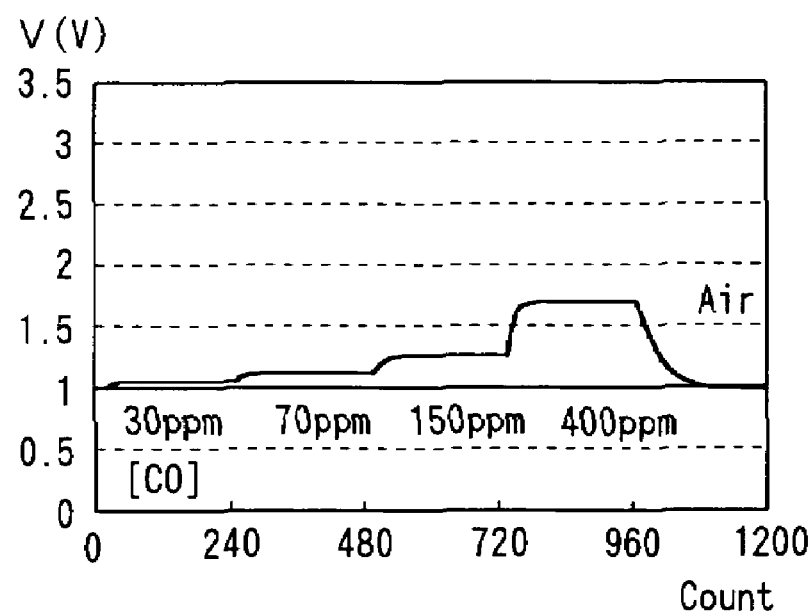
[FIG. 6] A diagram illustrating the sensitivity characteristics of an abnormal electrochemical gas sensor.
Figure 7:
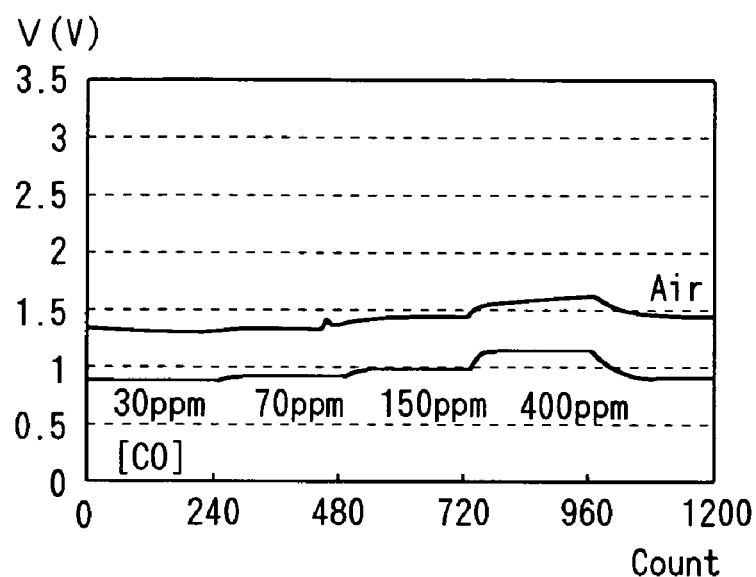
[FIG. 7] A diagram illustrating the sensitivity characteristics of another abnormal electrochemical gas sensor.
Figure 8:
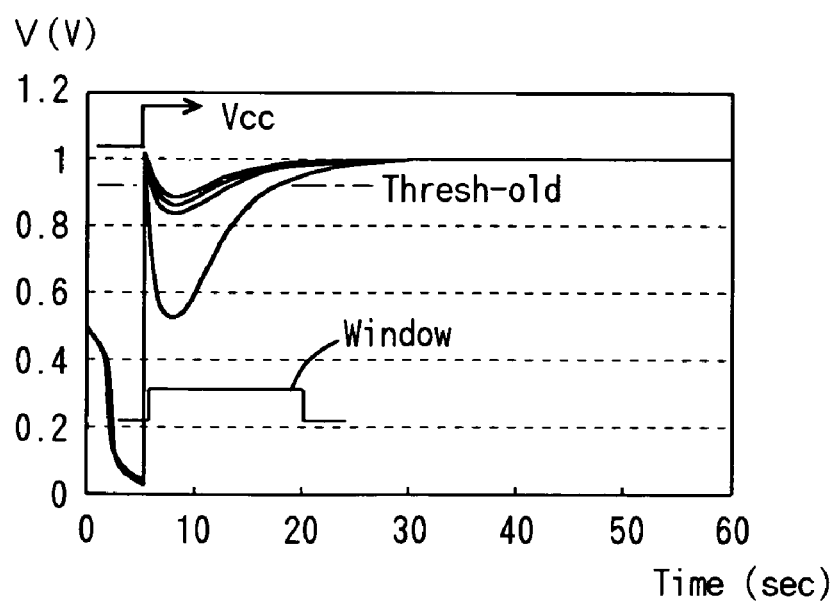
[FIG. 8] A diagram illustrating an output bottom that appears when the power source of the electrochemical gas sensor of FIG. 5 is turned on after that power source has been turned off for five seconds.
Figure 9:
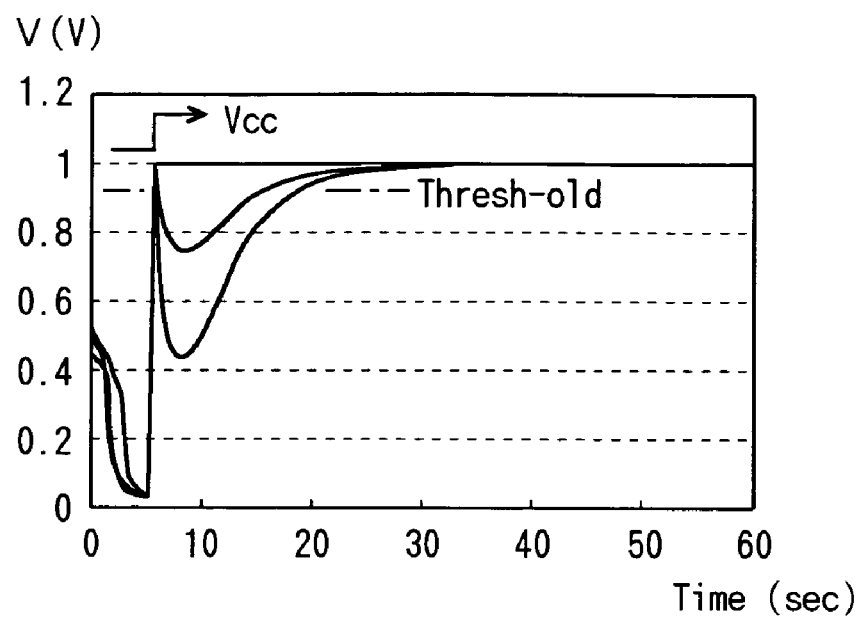
[FIG. 9] A diagram illustrating an output bottom that appears when the power source of the electrochemical gas sensor of FIG. 6 is turned on after that power source has been turned off for five seconds.
Figure 10:
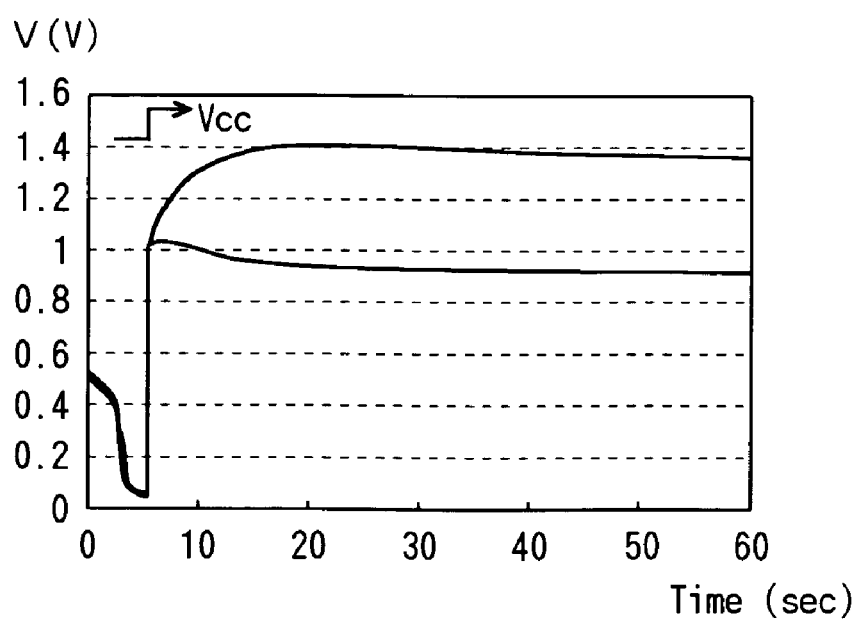
[FIG. 10] A diagram illustrating an output pattern that appears when the power source of the electrochemical gas sensor of FIG. 7 is turned on after that power source has been turned off for five seconds.

FIG. 5 through FIG. 7 illustrate sensitivity patterns (CO 30–400 ppm) of normal gas sensors (FIG. 5: number of sensors is 5) and defective gas sensors (FIG. 6: number of sensors is 3, FIG. 7: number of sensors is 2). FIG. 8 through FIG. 10 are output waveform diagrams when the power sources of these gas sensors and their incidental circuits are turned on again after the power sources have been turned off for five seconds. When the power sources are turned off for a short period, in the cases of the normal sensors, an output bottom (negative peak) will be generated, and this bottom is such an output waveform that the CO concentration to be sensed seems to become negative. With the use of this bottom, the defective sensors of FIG. 7 and the normal sensors of FIG. 5 can be distinguished from each other, however, it is hard to distinguish the defective sensors of FIG. 6 and the normal sensors of FIG. 5 from each other.

Figure 11:
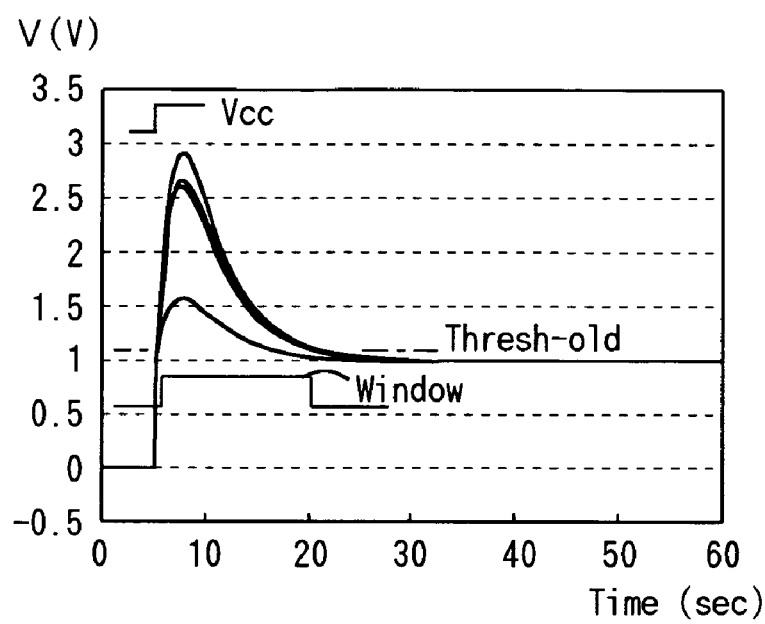
[FIG. 11] A diagram illustrating an output peak that appears when the power source of the electrochemical gas sensor of FIG. 5 is turned on after that power source has been turned off for one hour.
Figure 12:
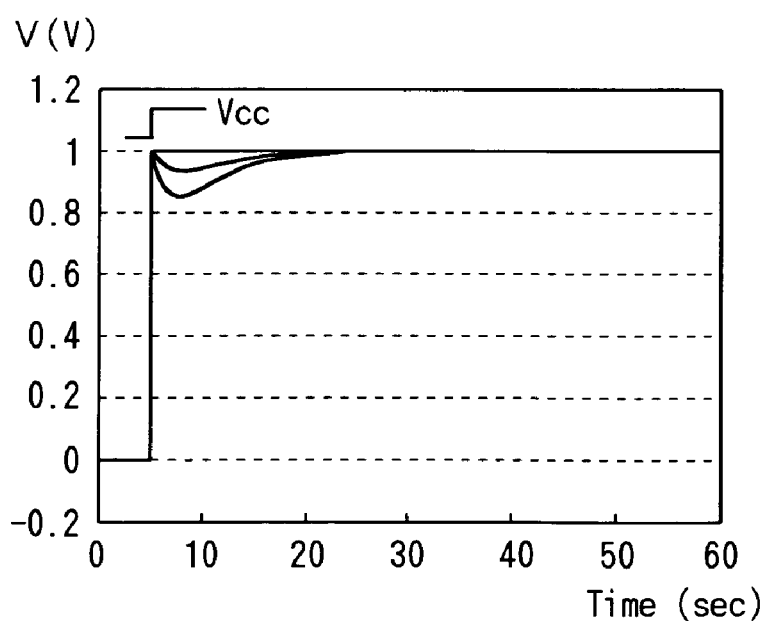
[FIG. 12] A diagram illustrating an output pattern that appears when the power source of the electrochemical gas sensor of FIG. 6 is turned on after that power source has been turned off for one hour.
Figure 13:
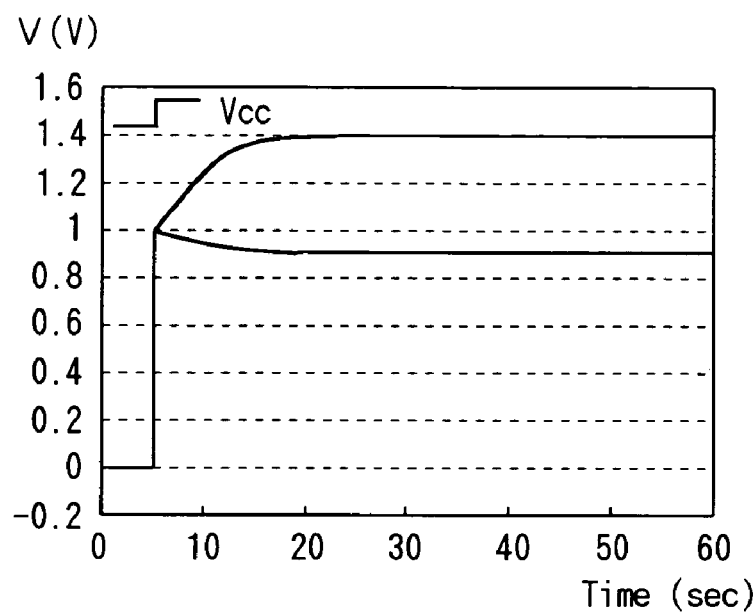
[FIG. 13] A diagram illustrating an output pattern that appears when the power source of the electrochemical gas sensor of FIG. 7 is turned on after that power source has been turned off for one hour.

FIG. 11 through FIG. 13 illustrate outputs when the power sources of the electrochemical gas sensors of FIG. 5 through FIG. 7 including their incidental circuits were turned on after the power sources had been turned off for one hour. In the cases of normal sensors, an output peak was generated, and in the cases of defective sensors, no peak was generated. Accordingly, whether a sensor is normal or defective can be judged reliably, but it involves a dead time of detection because the power source is turned off for a long period.

Figure 14:
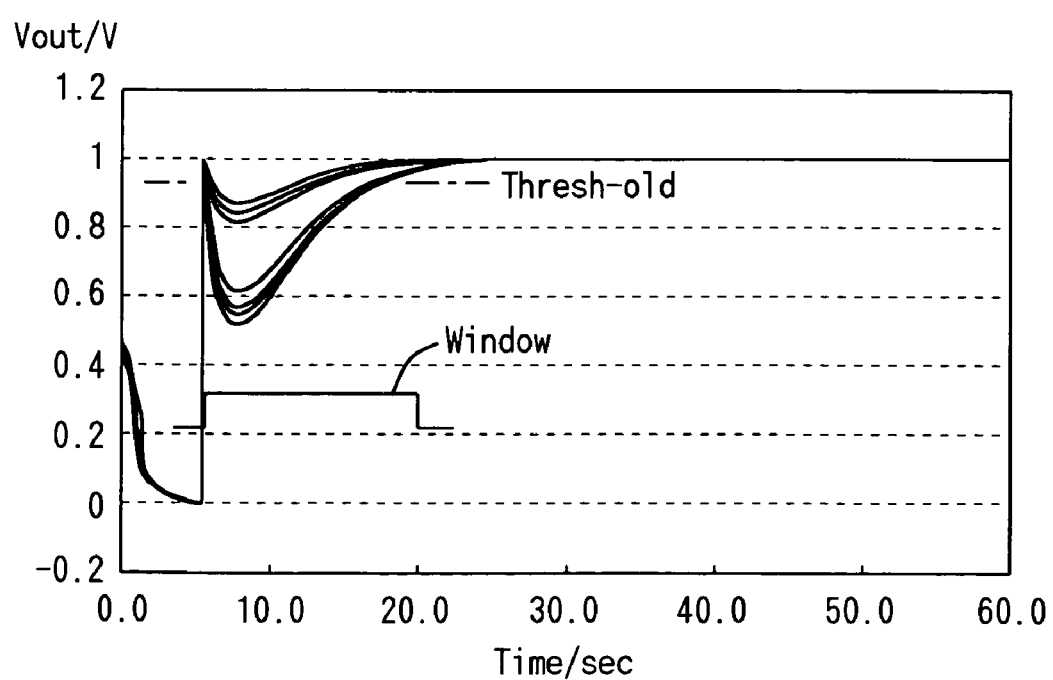
[FIG. 14] A diagram illustrating an output bottom that appears when the power source of a normal electrochemical gas sensor is turned on after that power source has been turned off for five seconds.
Figure 15:
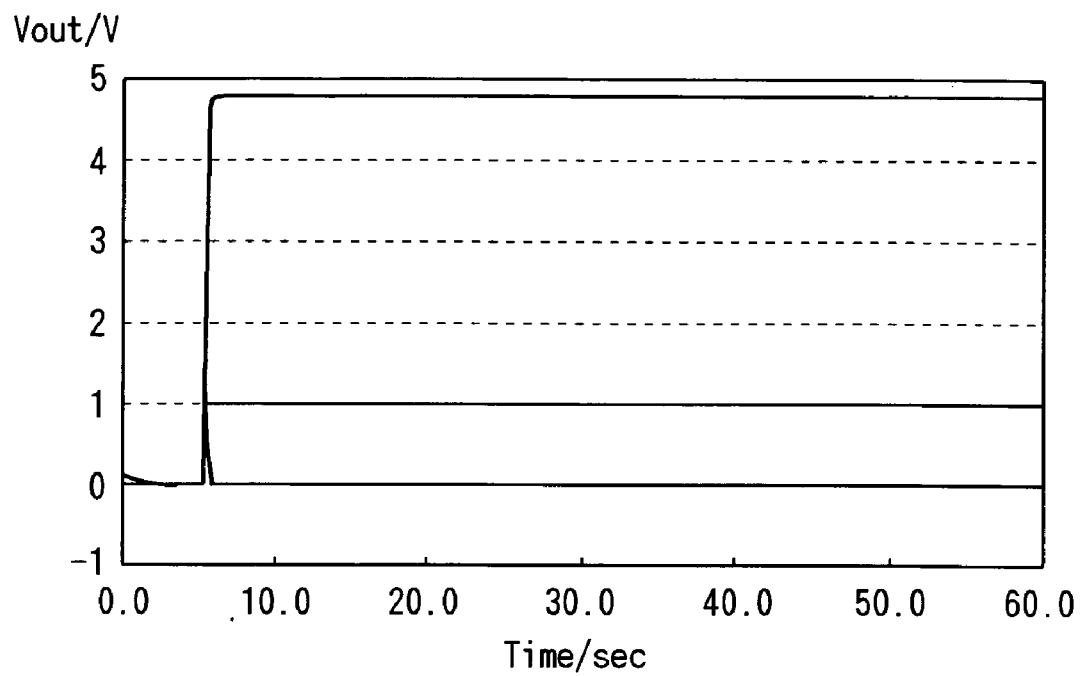
[FIG. 15] A diagram illustrating an output bottom that appears when the power source of an electrochemical gas sensor wherein a short-circuit or a disconnection is present is turned on after that power source has been turned off for five seconds.
Figure 16:
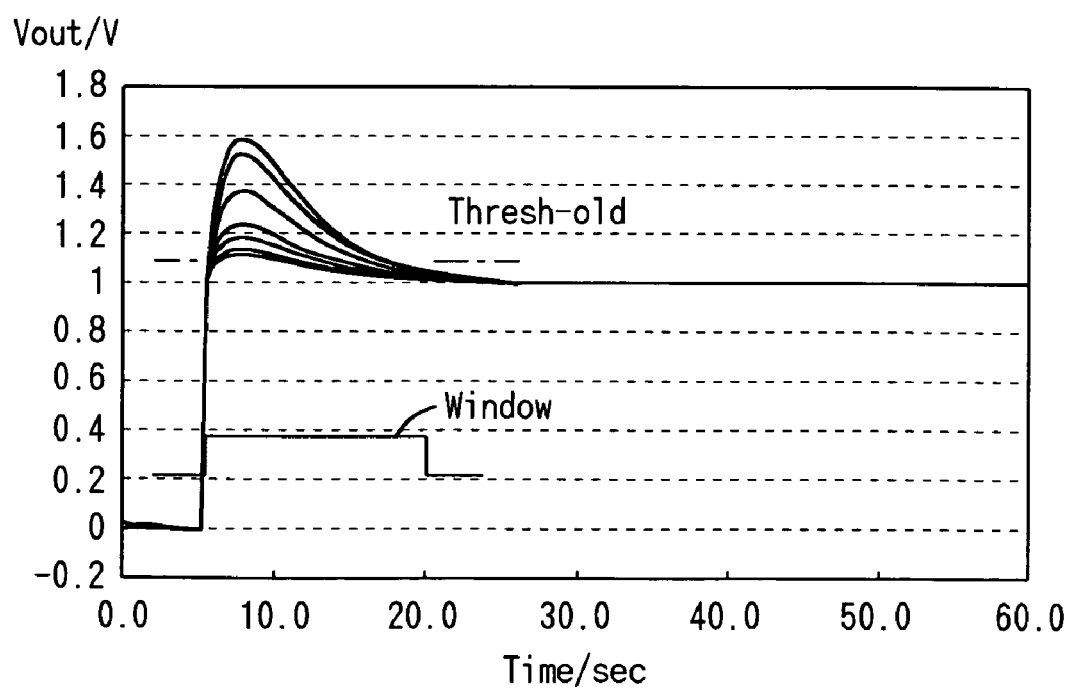
[FIG. 16] A diagram illustrating an output bottom when the power source of the electrochemical gas sensor of FIG. 14 is turned on after that power source has been turned off for five minutes.

FIG. 14 illustrates output waveforms when the power sources of twelve normal electrochemical gas sensors were turned on after the power sources had been turned off for five seconds. Each sensor showed an output bottom. FIG. 15 illustrates output waveforms under the same conditions of three sensors having a disconnection, short-circuit, etc. FIG. 16 illustrates output waveforms when the power sources of the gas sensors of FIG. 14 were turned on after the power sources had been turned off for five minutes. Although small in comparison with FIG. 11, all the sensors generated an output peak.

Figure 17:
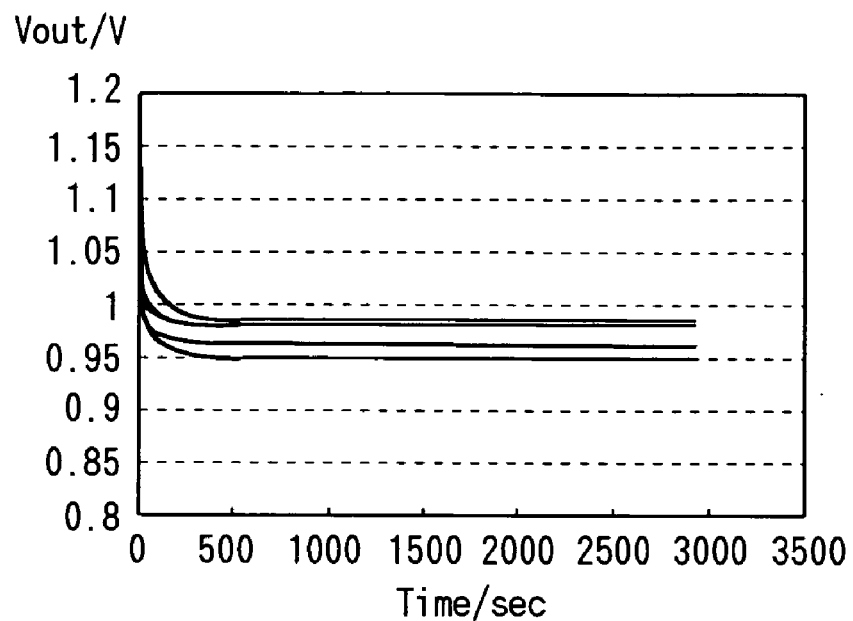
[FIG. 17] A response characteristic diagram when a voltage of 50 mV is applied between the sensing electrode and the counter electrode of the electrochemical gas sensor of FIG. 14 for four seconds.
Figure 18:
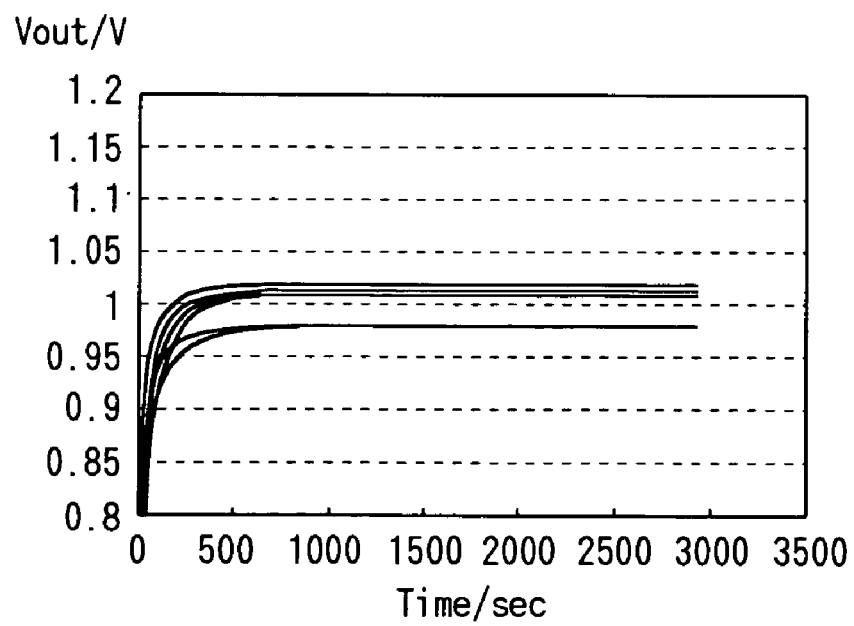
[FIG. 18] A response characteristic diagram when a voltage of 50 mV (the polarity is reverse to that of FIG. 17) is applied between the sensing electrode and the counter electrode of the electrochemical gas sensor of FIG. 14 for four seconds.

FIG. 17 and FIG. 18 illustrate output waveforms after voltage pulses of ±50 mV×4 seconds were applied between the sensing electrode and the counter electrode of eight normal electrochemical gas sensors. It took about 500 seconds for the output to return to the normal value. Hence the dead time of detection required for self-diagnosis is long.

In FIG. 1, 2 denotes a proton conductor gas sensor, and 4 denotes a sensor body comprising an MEA 10, a diffusion control plate 12, a upper housing 14 and a metal washer 28. In the MEA 10, as shown in the right of FIG. 1, a sensing electrode 43 and a counter electrode 44 are placed on both faces of a proton conductive membrane 42, and they are covered with electron-conductive carbon sheets 45, 46 (film thickness: about 40 μm). As for the proton conductive membrane 42, a membrane of a solid polymer electrolyte (SPE) of persulfonic acid type of which membrane thickness was about 20 μm, for example, one made by Gore, was used. As for both the sensing electrode 43 and the counter electrode 44, Pt was dispersed on carbon and the carbon was impregnated with an electrochemical polymer (membrane thicknesses were about 10 μm, respectively). It should be noted that the electron-conductive carbon sheets 45, 46 may be omitted. The materials, the membrane thickness, etc. of the MEA 10 are discretionary. The gas sensor 2 has two electrodes and is not provided with any reference electrode.

The diffusion control plate 12 is made of a thin plate of, for example, titanium, and its thickness is, for example, about 0.1 mm, and is provided with a diffusion control hole 26 of about 0.1 mm in diameter by punching or the like. The upper housing 14 is intended to eliminate on the upstream side of the diffusion control plate 12 poisonous materials and gases that may cause a false alarm, and it comprises a metal cap 16 and a metal bottom plate 18. A filtering material 20 comprising activated carbon, silica gel, zeolite, etc. for gas adsorption is filled between them.

The bottom plate 18 is provided with an opening 22 at, for example the central part thereof, the cap 16 is provided with an opening 24 on its side face, and the opening 22 and the opening 24 are so arranged that they do not overlap with each other in the axial direction of the upper housing 14. It is desirable that at least one type of the openings 22, 24 is provided in plurality. The washer 28 comprises a plate of metal such as stainless steel or titanium, and its thickness is greater in comparison with that of the diffusion control plate 12, for example, 0.5 mm. The washer 28 is provided with the water vapor introducing hole 30 at one place or a plurality of places to feed water vapor from the water reservoir to the counter electrode. The diameter of the water vapor introducing hole 30 is made larger than that of the diffusion control hole 26, for example, about 0.5 mm.

32 denotes a metal can, and here gel 34 that is pure water gelled is in the water reservoir. 36 denotes a concave that supports the metal washer 28, and 38 denotes a gasket that is arranged between the upper housing 14 and the metal can 32. The upper part of the metal can 32 is constricted to fix the sensor body on the metal can 32, and the upper housing 14 is insulated from the metal can 32 so that electric conductance and sealing are secured at various parts of the sensor body 4.

The CO detection mechanism will be described. The atmosphere that passes through the upper housing 14 goes through the diffusion control hole 26 to reach the sensing electrode 43. During this time, CO in the atmosphere will generate proton at the sensing electrode 43 by a reaction

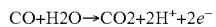
$$CO + H_2O \rightarrow CO_2 + 2H^+ + 2e^-$$

Water that is required for this reaction is supplied through the water vapor introducing hole. At the counter electrode 14, a reaction

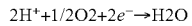
$$2H^+ + 1/2 O_2 + 2e^- \rightarrow H_2O$$

takes place. As the oxygen concentration in the atmosphere is significantly greater than the CO concentration therein, there is always oxygen that can completely oxidize CO at the counter electrode 44.

FIG. 2 illustrates the structure of the gas detecting device. 50 denotes a power source using a battery or the like. 51 denotes a reset switch. A power switch S1 that is normally open is intended to turn on or off the electric power to the gas sensor 2 and its amplification circuit. R1 through R10 denote resistances, and C1 through C5 denote capacitors. The power source of the amplifying circuit is denoted by +Vcc. The sensing electrode D and the counter electrode C of the gas sensor 2 are imaginary-short-circuited at both inputs of an operational amplifier IC2, and they are electrically connected when the power source of the operational amplifier IC2 is kept on.

A positive bias voltage that is determined by the ratio of the resistance R1 to the resistance R2, here +1 V, is applied, via an operational amplifier IC1, to the counter electrode C of the sensor 2 so as to make it easer to detect an output bottom. The major function of the operational amplifier IC1 is to eliminate ripples in the power source, and the operational amplifier IC1 may be omitted when a battery power source 50 is used. The current that flows from the sensing electrode D to the counter electrode C of the gas sensor 2 is transformed by the resistor RS into a voltage. The internal resistance between the sensing electrode D and the counter electrode C is about 1 ohm, and the resistance of the resistor RS is about 100 kΩ. In the operational amplifier IC3, amplification is made by a factor that is determined by the resistance ratio of the resistor R6 and the resistor R8. Here, the resistor R6 is set at about 3 kΩ and the resistor R8 is set at about 100 kΩ. As a result, when a current of 1 nA flows from the sensing electrode D to the counter electrode C, the output voltage Vout of the operational amplifier IC3 will be 3 mV. For example, when CO 600 ppm is present, the output of the operational amplifier IC3 will increase from zero gas level by 3 V, and in the gas sensor 2 a current of about 1 μA will flow from the sensing electrode D to the counter electrode C. The resistor R9 that is connected to the operational amplifier IC3 is a resistor for adjusting the output Vout to 1 V at the zero gas level.

The resistor R10 is a resistor of about 1 kΩ, and is parallel-connected to the gas sensor 2 together with the switch S2 that is normally closed. The resistor R10 is a resistor that prevents the gas sensor 2 from polarization when the gas detecting device is in stock or the like, and the resistor R10 and the switch S2 may be omitted. The resistance of the resistor R10 is extremely higher than the resistance of the gas sensor 2, and its effects on the gas detection signals are negligible. The switch S2 is opened when the switch S1 is opened for self-diagnosis of the gas sensor 2, and the switch S2 is closed during the subsequent period of observing a bottom or a peak. However, the switch S2 may be kept open during the period of observing a bottom or a peak. The resistor R10 and the switch S2 may be omitted.

In the embodiment, current amplification is effected in two stages or with the operational amplifiers IC2 and IC3, but current amplification can be made in a single stage. In the embodiment, a bias potential of +1V is applied to the counter electrode C, but the bias potential can be varied, for example, in a range of from about 100 mV to about 2 V. In place of using a single power source such as ±5V as the circuit power source +Vcc, if a dual power source such as ±5V is used to drive the operational amplifiers IC1 through IC3, the bias potential can be set, for example, at zero. In the embodiment, self-diagnosis is made by using phenomena such as occurrence of polarization or local potential or mixed potential between the sensing electrode D and the counter electrode C rather than the capacitance between the sensing electrode D and the counter electrode C.

The amplifying circuit of the gas sensor 2 comprises resistors R1 and R2 through R10, operational amplifiers IC1 through IC3, etc. Signal processing of the output signal Vout is done by a microcomputer 54. 55 denotes an AD converter, 56 denotes a CO detector that computes out the CO concentration by comparing the output Vout with predetermined thresholds. 57 denotes a self-diagnosing part that self-diagnoses the gas sensor 2 from the transient waveforms of the output Vout when the power source 50 is turned on after the power source 50 has been turned off for a predetermined time. Moreover, the self-diagnosing part can inspect the amplifying circuit because if the amplifying circuit is defective, the output Vout reads an abnormal value.

58 denotes a power controller that turns on and off the switch S1. The microcomputer 54 has two modes, namely, operation mode and standby mode. In the standby mode, the microcomputer 54 operates, for example, a timer 68 only to control the standby time and suspend all others except supplying electric power to an RAM 69 to store data. When the microcomputer 54 shifts to the standby mode, it will open the switch S1 in synchronization to cut electric power supply to the gas sensor 2 and the amplifying circuit. When the timer 68 turns off the switch S1 for a predetermined time, the microcomputer 54 will shift from the standby mode to the operation mode, and in synchronization with the shift, the microcomputer 54 will close the switch S1 to turn on the power source of the gas sensor 2 and its amplifying circuit. Then self-diagnosis of the gas sensor 2 will be done from the waveform for a predetermined time, for example, from about 5 seconds to 15 seconds, after the power source is turned on.

59 denotes an LED drive that drives an LED group 60 comprising a plurality of LEDs. The display states of the LED group 60 include, for example, four kinds, namely, "normal," "the gas detecting device is not operating properly," "CO of low concentration is present," and "CO of high concentration is present." A buzzer drive 61 drives a buzzer 62; it drives the buzzer 62, for example, when CO of high concentration is present or when CO of low concentration is present for a period exceeding a permissible time. An LCD drive 63 drives an LCD 64 to display CO concentration, "the gas detecting device is not operating properly," "resetting is needed," etc.

An EEPROM 65 is intended to store primary data even if the power source is turned off by the reset switch 51. Such primary data include history of CO detection, history of self-diagnosis of the gas detecting device, and total hours of use of the power source. A reset controller 66 initializes the microcomputer 54 when the power source is turned on by the reset switch 51. A battery checker 67 checks the value of the circuit power source +Vcc, etc. and checks whether replacement of the power source 50 is needed. The battery checker 67 is inputted with the circuit power source +Vcc via an AD converter that is not illustrated.

The timer 68 determines a variety of operation periods of the microcomputer 54, in particular, it determines the open/close period of the switch S1. For example, the switch S1 is opened for 40 seconds, then the switch S1 is closed for 20 seconds; thus the switch S1 is driven for a period of 60 seconds. Of the ON time of 20 seconds of the switch, the first 15 seconds are used for self-diagnosis of the gas sensor 2, and the last 5 seconds are used for CO detection. The gas sensor 2 normally operates with one minute period, and for example, once in every month the switch S1 is turned off for a period longer than above-mentioned one minute period, for example, one hour, and the self-diagnosis of the gas sensor 2 is done by using a period of 15 seconds after the switch S1 is turned on from its off state. As mentioned earlier, when the switch S1 is open, the microcomputer 54 is also in its standby mode. The RAM 69 stores a variety of data that are needed for the operation of the microcomputer 54.

FIG. 3 illustrates the operation of the gas detecting device in the course of the self-diagnosis. The switches S1, S2 are periodically opened for predetermined periods to break the connection between the sensing electrode and the counter electrode. Next, the switch S1 is closed to detect whether an output bottom or peak is generated in a predetermined period. During this detection period, it does not matter whether the switch S2 is closed or open.

FIG. 4 illustrates the self-diagnosis algorithm of the embodiment. When the period for turning off the switch S1 is not over one minute, for example, when it is 40 seconds in the case of the embodiment, checking for abnormality is made on the basis of presence or absence of an output bottom after the switch S1 is turned on. When the off time is, for example, over five minutes, checking for abnormality is made on the basis of presence or absence of an output peak after the switch S1 is turned on from its off state. In the embodiment, the longer off time of the power source is, for example, one hour. Preferably, the longer off time of the power source is, for example, from 3 minutes to 24 hours, and more preferably, from five minutes to 12 hours, and much more preferably, from five minutes up to one hour. Preferably, the shorter off time of the power source is, for example, from 1 minute down to 0.1 second, more preferably, from 1 minute down to one second, and much more preferably, from 40 seconds down to 3 seconds. A boundary between the long off time and the short off time is, for example, 3 minutes, and a time longer than 3 minutes is defined as, for example, exceeding a predetermined time, and a time shorter than 3 minutes is defined as, for example, less than a predetermined time.

If any abnormality is detected in the gas sensor, that information will be stored in the EEPROM and the RAM. If an abnormality is detected after the short off time, the power source is turned off again automatically by the switch S1, for example, for 40 seconds to repeat the self-diagnosis. In this way, if the abnormality is detected, for example, twice, a request for reset, etc. will be displayed on the LCD 64. If the presence of an abnormality is recorded in the EEPROM and a reset is done, during the recovery from the reset, the switch S1 is turned off, for example, for five minutes to forcibly execute the long off time. The subsequent output pattern is checked for abnormality, and if the abnormality is confirmed, a record, for example, of a permanent defect will be stored in the EEPROM, and the displays on the LED 60 and the LCD 64 will be maintained.

If an abnormality is detected after the long off time of the switch S1, the information of the abnormality will be similarly stored in the EEPROM, and resetting will be demanded. After the resetting, the power source will be turned off by opening the switch S1 again for the long time, and if an abnormality is detected again, a record, for example, of a permanent defect will be stored in the EEPROM, and that information will be displayed by the LCD and the LEDs.

If no abnormality is detected, or if an abnormality is detected but the abnormality is not detected again after the resetting, CO detection will be made, and the power source will be turned off every predetermined time to shift to the standby mode.

FIG. 5 illustrates the output waveforms of five normal gas sensors, and the current that flows from the sensing electrode D to the counter electrode C is 0.7 μA for CO 400 ppm. The sensor output is proportional to the CO concentration. FIG. 6 illustrates the waveforms of three sensors, and the waveforms of two sensors overlap on the output 1 V line. These sensors are defective in CO sensitivity or do not show CO sensitivity. FIG. 7 illustrates the waveforms of two gas sensors, and they are abnormal in their zero levels and their CO sensitivities are low.

FIG. 8 through FIG. 10 illustrate the characteristics of these gas sensors when the power source is turned on again after the power source has been turned off for five seconds by opening the switch S1. In the case of the normal gas sensors of FIG. 5 and in the case of the two gas sensors among the abnormal gas sensors of FIG. 6 (FIG. 9), an output bottom will appear when the power source is turned on. In contrast to them, in the case of the gas sensors of FIG. 7, no output bottom will appear (FIG. 10).

To detect a bottom, it is sufficient to set a threshold, for example, at 0.95 V that is lower by 50 mV from the bias potential and detect that, for example, in a window within 15 seconds after turning on the power source, the output passes the threshold from above downward and then passes the threshold from below upward. Otherwise, after the power source is turned on and the output marks a peak of 1 V, the time derivative of the output voltage may be used. The method of detecting the output bottom itself is discretionary.

FIG. 11 through FIG. 13 illustrate the characteristics of the gas sensors of FIG. 5 through FIG. 7 when the power source is turned on again after the power source has been turned off for one hour. The power source is turned on when the time is 5 second. As for the gas sensors of FIG. 5, all the sensors mark an output peak. In contrast to them, as for the gas sensors of FIG. 6, the sensors do not show any output peak, and when the time for turning off the power source is made longer, the gas sensors of FIG. 5 and the gas sensors of FIG. 6 can be distinguished from each other. As for the gas sensors of FIG. 7, irrespective whether the power source off time is long or short, the sensors show the same behavior (FIG. 10, FIG. 13).

FIG. 14 illustrates the characteristics of normal 12 gas sensors when the power source is turned on after the power source has been turned off for five seconds. Every sensor shows an output bottom when the power source is turned on from its off state. The gas sensors of FIG. 15 have defects such that the sensing electrode and the counter electrode are short-circuited or the sensing electrode or the counter electrode is off its terminal. In such cases, the output waveforms are of three kinds, namely, 1 V of the bias voltage appears as it is, 0 V of the earth voltage appears as it is, and 5 V of the circuit voltage +Vcc appears as it is. In any case, any transient waveform does not appear when the power source is turned on from its off state.

FIG. 16 illustrates the waveforms of the 12 normal sensors of FIG. 14 when the power source is turned on after the power source has been turned off for five minutes. When the power source was turned on from the off state, all the 12 sensors showed an output peak. The threshold was set at the bias potential plus 100 mV.

As described so far above, self-diagnosis of the electrochemical gas sensor 2 can be done on the basis of the transient waveform when the power source is turned on from its off state. When the off time of the power source is short, for example, when it is five seconds, an output bottom will appear in the transient waveform. When the on time of the power source is long, for example, when it is five or more minutes, an output peak will appear. Of these two self-diagnoses, one with the longer off time of the power source has a higher reliability. However, when the off time of the power source is made longer, the dead time of CO detection will become longer. Accordingly, it is better to conduct both the self-diagnosis with a short off time and the self-diagnosis with a long off time, and conduct the self-diagnosis with the short off time at a relatively high frequency and the self-diagnosis with the long off time at a relatively low frequency. Turning off the power source, which is required for self-diagnosis, may be done by using the standby mode that is intended to give a rest to the battery power source 50.

FIG. 17 and FIG. 18 illustrate the waveforms of other eight normal electrochemical gas sensors after applying them potentials of ±50 mV for four seconds. FIG. 17 illustrates waveforms when the sensing electrode was + and a voltage of 50 mV was applied between the sensing electrode and the counter electrode. Conversely, FIG. 18 illustrates waveforms when a voltage of −50 mV was applied to the sensing electrode.

When the voltage of 50 mV×4 seconds is applied, the sensor signal will not be stabilized for about 500 seconds after that. Hence the dead time of detection will get longer. Next, when a voltage of 50 mV is applied between the sensing electrode and the counter electrode, a current of 10 mA or over will flow between both the electrodes. As the gas sensor 2 is designed to flow a current of about 1 µA for CO 600 ppm, if a current of 10 mA or over flows, there is a possibility that the interfaces between the electrodes and the proton conductive membrane might be affected or its hysteresis might remain.

As explained above, in the embodiment, the self-diagnosis of the electrochemical gas sensor can be conducted by utilizing turning on/off of the power source between its standby mode and operation mode. The self-diagnosis is not limited to detection of simple defects such as short-circuit. Deficient sensitivity and floating of the sensor output can be detected as well.

Figure 19:
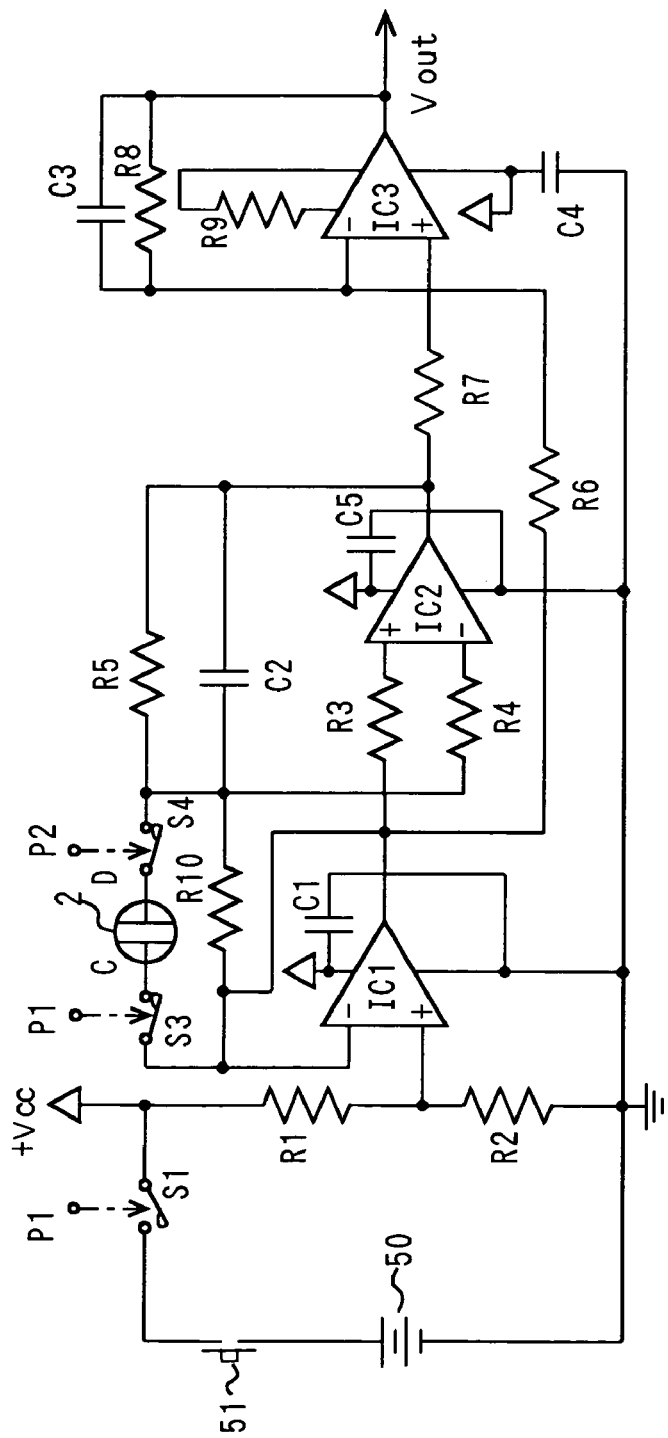
[FIG. 19] A block diagram of a modification of the electrochemical gas detecting device.

FIG. 19 illustrates an example wherein a switch S4 and a switch S3 are connected to the sensing electrode D and the counter electrode C of the gas sensor 2, respectively, and the connection between the sensing electrode and the counter electrode is opened and closed, through the switches S3, S4, by a control signal P2 from the microcomputer. In this example, opening/closing of a switch S1 for saving power by a control signal P1, and opening/closing of switches S3, S4 for self-diagnosis can be done independently. This modification is similar to the embodiment of FIG. 1 through FIG. 18 in other aspects, and the same marks denote the same things, and the microcomputer 54 of FIG. 2 is connected to the output side of the operational amplifier IC3.

The gas sensor is not limited to the proton conductor gas sensor and may be a liquid electrolyte gas sensor using an electrolyte such as sulfuric acid electrolyte, alkaline electrolyte, simple water or ionic liquid; the kind of electrolyte is discretionary. The present inventor have confirmed that characteristics similar to those of FIG. 8 through FIG. 18 can be obtained for a gas sensor using 0.1 N KOH aquatic solution as its electrolyte.

The invention claimed is:

1. A self-diagnostic method for an electrochemical gas sensor having an electrolyte, a sensing electrode, and a counter electrode, comprising:
    a step for connecting the sensing electrode and the counter electrode via an amplifying circuit;
    a step for opening the connection of the sensing electrode and the counter electrode;
    a step for reconnecting the sensing electrode and the counter electrode; and
    a step for self-diagnosing said gas sensor as normal when an output bottom of said amplifying circuit is present and as defective when said output bottom of said amplifying circuit is absent.

2. A self-diagnostic method for an electrochemical gas sensor according to claim 1,
    at a first frequency, performing the step for opening the connection for a period shorter than a predetermined period, performing the step for reconnecting the sensing electrode and the counter electrode, and performing the step for self-diagnosing said gas sensor according to whether the output bottom is present, and at a second frequency lower than the first frequency, performing the step for opening the connection for a period longer than the predetermined period, performing the step for reconnecting the sensing electrode and the counter electrode, and performing the step for self-diagnosing said gas sensor according to whether an output peak of the amplifying circuit is present.

3. The self-diagnostic method for an electrochemical gas sensor according to claim 1, wherein said step for opening the connection is performed at a frequency and includes opening the connection for a period shorter than a predetermined period.

4. The self-diagnostic method for an electrochemical gas sensor according to claim 3, wherein said frequency is about once a minute and said predetermined period is about three minutes.

5. The self-diagnostic method for an electrochemical gas sensor according to claim 3, wherein said period is about 40 seconds to one minute.

6. The self-diagnostic method for an electrochemical gas sensor according to claim 1, wherein said step for opening the connection is performed at a frequency and includes opening the connection for a period longer than a predetermined period.

7. The self-diagnostic method for an electrochemical gas sensor according to claim 6, wherein said frequency is about once a month and said predetermined period is about three minutes.

8. The self-diagnostic method for an electrochemical gas sensor according to claim 6, wherein said period is about five minutes to one hour.

9. The self-diagnostic method for an electrochemical gas sensor according to claim 1, wherein said output bottom is present if an output voltage is detected that passes a threshold voltage from above downward and then passes the threshold voltage from below upward, the threshold voltage being about 50 mV lower than a bias potential voltage of the gas sensor.

10. A gas detecting device comprising an electrochemical gas sensor having an electrolyte, a sensing electrode, and a counter electrode, the sensing electrode and the counter electrode being connected via an amplifying circuit, said gas detecting device further comprising:
a switch opening and closing the connection between the sensing electrode and the counter electrode;
self-diagnostic means for making the switch open for a first period shorter than a predetermined period, making the switch close, detecting a bottom in the output of the amplifying circuit, and judging the gas sensor normal when said bottom is detected and judging the gas sensor defective when said bottom is not detected; and
display means for displaying the judgment.

11. A gas detecting device according to claim 10, said self-diagnostic means having:
means for making, at a first frequency, the switch open for said first period shorter than the predetermined period and the switch close; and at a second frequency lower than the first frequency, the switch open for a second period longer than the predetermined period and the switch close, and
said self-diagnostic means judging said gas sensor according to whether the output bottom is present after the first period, and further judging said gas sensor according to whether the output peak is present after the second period.

12. A gas detecting device according to claim 10, said switch being a power switch of said amplifying circuit or a switch electrically connecting and disconnecting said gas sensor to said amplifying circuit.

13. The gas detecting device according to claim 10, wherein said predetermined period is about three minutes.

14. The gas detecting device according to claim 10, wherein said first period is about 40 seconds to one minute.

15. The gas detecting device according to claim 10, wherein said output bottom is detected if an output voltage is detected that passes a threshold voltage from above downward and then passes the threshold voltage from below upward, the threshold voltage being about 50 mV lower than a bias potential voltage of the gas sensor.

16. A self-diagnostic method for an electrochemical gas sensor having an electrolyte, a sensing electrode, and a counter electrode, comprising:
a step for connecting the sensing electrode and the counter electrode via an amplifying circuit;
a step for opening the connection of the sensing electrode and the counter electrode;
a step for reconnecting the sensing electrode and the counter electrode; and
a step for self-diagnosing said gas sensor according to whether an output peak or an output bottom of said gas sensor is present, wherein
at a first frequency, performing the step for opening the connection for a period shorter than a predetermined period, performing the step for reconnecting the sensing electrode and the counter electrode, and performing the step for self-diagnosing said gas sensor according to whether the output bottom is present, and
at a second frequency lower than the first frequency, performing the step for opening the connection for a period longer than the predetermined period, performing the step for reconnecting the sensing electrode and the counter electrode, and performing the step for self-diagnosing said gas sensor according to whether the output peak is present.

17. A gas detecting device including an electrochemical gas sensor having an electrolyte, a sensing electrode, and a counter electrode, the sensing electrode and the counter electrode being connected via an amplifying circuit, the gas detecting device comprising:
a switch opening and closing the connection between the sensing electrode and the counter electrode;
self-diagnostic means for making the switch open, making the switch close, detecting a peak or a bottom in the output of the amplifying circuit, and judging the gas sensor normal when said bottom or said peak is detected and judging the gas sensor defective when said bottom or said peak is not detected;
display means for displaying the judgment; and
means for making, at a first frequency, the switch open for a first period shorter than a predetermined period and the switch close; and at a second frequency lower than the first frequency, the switch open for a second period longer than the predetermined period and the switch close, wherein
said self-diagnostic means judging said gas sensor according to whether the output bottom is present after the first period, and further judging said gas sensor according to whether the output peak is present after the second period.

* * * * *